United States Patent
Kobayashi et al.

(10) Patent No.: US 9,138,152 B2
(45) Date of Patent: Sep. 22, 2015

(54) ELECTRONIC BLOOD PRESSURE METER

(71) Applicant: OMRON HEALTHCARE Co., Ltd., Kyoto (JP)

(72) Inventors: Tatsuya Kobayashi, Kyoto (JP); Yuki Yamashita, Kyoto (JP); Yoshihiko Sano, Kyoto (JP); Yukiya Sawanoi, Kyoto (JP); Hironori Sato, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 14/350,373

(22) PCT Filed: Oct. 10, 2012

(86) PCT No.: PCT/JP2012/076232
§ 371 (c)(1),
(2) Date: Apr. 8, 2014

(87) PCT Pub. No.: WO2013/061780
PCT Pub. Date: May 2, 2013

(65) Prior Publication Data
US 2014/0316290 A1  Oct. 23, 2014

(30) Foreign Application Priority Data

Oct. 26, 2011 (JP) ................................. 2011-235018

(51) Int. Cl.
*A61B 5/02* (2006.01)
*A61B 5/021* (2006.01)
(Continued)

(52) U.S. Cl.
CPC ........... *A61B 5/02141* (2013.01); *A61B 5/0225* (2013.01); *A61B 5/02225* (2013.01); *A61B 5/107* (2013.01)

(58) Field of Classification Search
None
See application file for complete search history.

(56) References Cited

U.S. PATENT DOCUMENTS

2011/0152650 A1\* 6/2011 Donehoo et al. ............... 600/324
2012/0220884 A1\* 8/2012 Yamashita et al. ............ 600/490
2012/0232412 A1\* 9/2012 Kinoshita et al. ............. 600/498

FOREIGN PATENT DOCUMENTS

CN  201831887 U  5/2011
JP  62-155828 A  7/1987
(Continued)

OTHER PUBLICATIONS

International Search Report for corresponding International Application No. PCT/JP2012076232, mailed Dec. 4, 2012 (4 pages).
(Continued)

*Primary Examiner* — Etsub Berhanu
(74) *Attorney, Agent, or Firm* — Osha Liang LLP

(57) ABSTRACT

A blood pressure meter includes an adjustment unit that adjusts a pressure in a cuff by controlling a piezoelectric pump that uses a piezoelectric vibrator to supply fluid to the cuff, a driving control unit that gradually changes a cuff pressure by performing driving control on the adjustment unit, a pressure detection unit that detects the cuff pressure, a blood pressure determination unit that determines a blood pressure value, a circumferential length detection unit that detects a circumferential length of the measurement area, a battery that supplies power to various units, and a decrease detection unit that detects a voltage decrease value for the battery during blood pressure measurement. Based on the circumferential length and the voltage decrease value detected in an initial inflation period when the blood pressure measurement is first started, a range of the voltage decrease value during blood pressure measurement carried out thereafter is estimated.

12 Claims, 6 Drawing Sheets

(51) Int. Cl.
*A61B 5/0225* (2006.01)
*A61B 5/022* (2006.01)
*A61B 5/107* (2006.01)

(56) References Cited

FOREIGN PATENT DOCUMENTS

| JP | 04-158833 A | 6/1992 |
| JP | 5-42114 A | 2/1993 |
| JP | 2008-188197 A | 8/2008 |
| JP | 2009-74418 A | 4/2009 |
| JP | 2009-225842 A | 10/2009 |
| WO | 2009/093514 A1 | 7/2009 |
| WO | 2009/142266 A1 | 11/2009 |
| WO | WO 2011058927 A1 * | 5/2011 |
| WO | WO 2011062154 A1 * | 5/2011 |
| WO | WO 2011101759 A1 * | 8/2011 |

OTHER PUBLICATIONS

Written Opinion for corresponding International Application No. PCT/JP2012/076232, mailed Dec. 4, 2012 (7 pages).
Office Action issued in counterpart Chinese Patent Application No. 201280048090.0 dated Feb. 16, 2015 (15 pages).

* cited by examiner

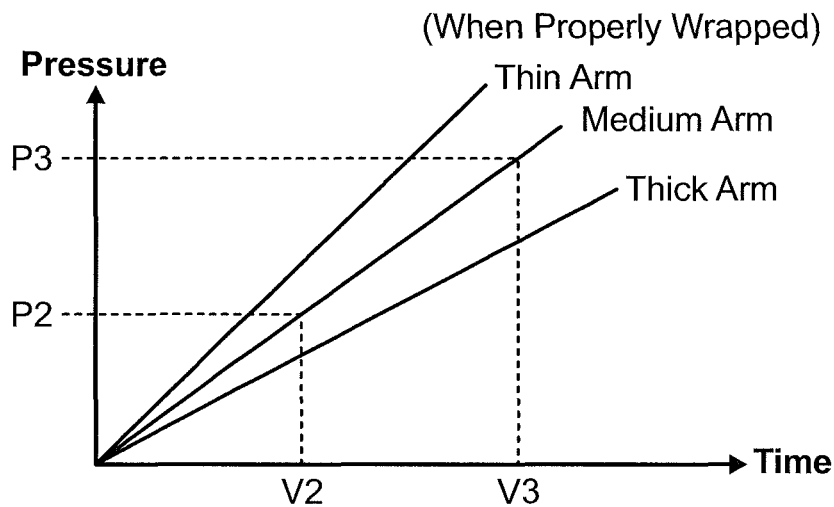
FIG. 4
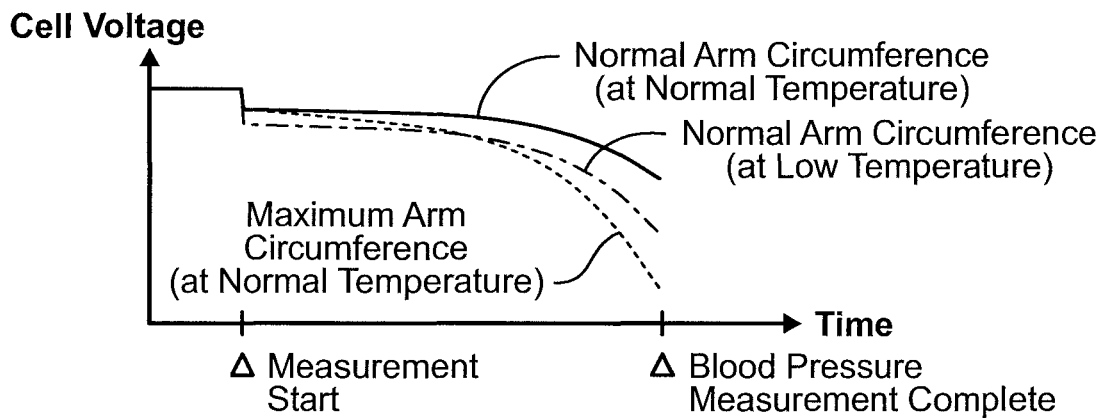
FIG. 5
| Decrease Value | Temperature |
|---|---|
| x x ~ x △ | Low Temperature |
| x △ ~ x ○ | Normal Temperature |
| x ○ ~ ○ ○ | High Temperature |
FIG. 6

(Normal Temperature) 435
(Low Temperature) 435
435 (High Temperature)

| Circumferential Length | | Voltage Decrease Formula | Consumed Power Calculation Formula |
|---|---|---|---|
| Small | L(1)~L(2) | F△O | W1 |
| Normal | L(3)~L(4) | F△△ | W2 |
| Large | L(5)~L(6) | FOO | W3 |

ELECTRONIC BLOOD PRESSURE METER

TECHNICAL FIELD

The present invention relates to electronic blood pressure meters, and particularly relates to electronic blood pressure meters that measure a blood pressure using pulse waves detected from a measurement area.

BACKGROUND ART

Blood pressure is one index for analyzing cardiovascular disease, and performing a risk analysis based on blood pressure is effective in preventing cardiovascular-related conditions such as stroke, heart failure, and myocardial infarction. Thus far, diagnoses have been made using blood pressure (casual blood pressure) measured at medical institutions, such as during hospital visits, health checkups, and so on. However, recent research has shown that blood pressure measured at home (home blood pressure) is more useful in diagnosing cardiovascular disease than casual blood pressure. As a result, blood pressure meters for use at home are becoming widespread.

Many household blood pressure meters employ an oscillometric blood pressure measurement technique. When measuring blood pressure using the oscillometric technique, a cuff is wrapped around a measurement area such as an upper atm, the cuff is inflated until the internal pressure thereof (a cuff pressure) reaches a pressure higher than a systolic blood pressure by a predetermined pressure (for example, 30 mmHg), and the cuff pressure is then reduced gradually or in steps. As the pressure is being reduced, a change in the volume of the artery is detected as a change in the pressure superimposed on the cuff pressure (a pulse wave amplitude), and the systolic blood pressure and diastolic blood pressure are determined based on the change in the pulse wave amplitude. Furthermore, with the oscillometric technique, it is possible to measure the blood pressure by detecting a pulse wave amplitude occurring while the cuff pressure is being increased.

To accurately detect the pulse wave amplitude in such blood pressure measurements, it is necessary to increase or decrease the cuff pressure at a constant speed using a pump or a valve. Specifically, feedback control is executed on a driving voltage for a pump or a valve during constant speed inflation control or constant speed deflation control based on a difference between an average speed and a target speed, so that the average speed reaches the target speed. A pump that uses a motor as its driving source, a piezoelectric micro pump that uses a piezoelectric element as its driving source, or the like can be employed as blood pressure measurement pump that undergoes feedback control. Patent Literature 1 (JP 2009-74418A), for example, discloses a piezoelectric micro pump structure.

Meanwhile, Patent Literature 2 (JP H5-42114A) discloses a method for determining an inflation speed based on a cell voltage as a method for determining a pump inflation speed.

CITATION LIST

Patent Literature

Patent Literature 1: JP 2009-74418A
Patent Literature 2: JP H5-42114A

SUMMARY OF INVENTION

Technical Problem

The method for determining the inflation speed based on the cell voltage according to Patent Literature 2 does not take into consideration a decrease in the cell voltage during the blood pressure measurement. In other words, pumps that consume a large amount of power experience a higher decrease in cell voltage, and it is thus difficult to determine the inflation speed with accuracy.

Meanwhile, with a piezoelectric micro pump, in the case where the piezoelectric element has not been completely broken but the impedance of the piezoelectric element has changed due to cracks caused by the impact of the device being dropped or the like, a large amount of power will be consumed despite the pump not being completely broken. Continuing to use the pump in such a state will shorten the lifespan of the battery, and the pump will malfunction and the device will be rendered unusable.

Accordingly, it is an object of the present invention to provide an electronic blood pressure meter capable of estimating a greater power consumption than was initially assumed.

Solution to Problem

An electronic blood pressure meter according to an aspect of this invention includes a cuff to be wrapped around a measurement area of a measurement subject, an adjustment unit for adjusting a pressure in the cuff by controlling a piezoelectric pump that uses a piezoelectric vibrator to supply a fluid to the cuff, a driving control unit for gradually changing the pressure in the cuff by performing driving control on the adjustment unit, a pressure detection unit for detecting a cuff pressure indicating the pressure in the cuff, a blood pressure determination unit for determining a blood pressure value based on the cuff pressure detected by the pressure detection unit, a circumferential length detection unit for detecting a circumferential length of the measurement area, a battery for supplying power to various units, and a decrease detection unit for detecting a voltage decrease value for the battery during blood pressure measurement; here, based on the circumferential length and the voltage decrease value detected in an initial inflation period when the blood pressure measurement is first started, a range of the voltage decrease value during blood pressure measurement carried out thereafter is estimated.

Advantageous Effects of Invention

According to the present invention, it is possible, based on a circumferential length and a voltage decrease value detected in an initial inflation period when blood pressure measurement is first started, to estimate a greater power consumption than was initially assumed by estimating a range of values for a decrease in voltage during the blood pressure measurement carried out thereafter.

BRIEF DESCRIPTION OF DRAWINGS

FIG. 4 illustrates a graph showing cuff pressure-inflation time properties (when properly wrapped) according to the embodiment.

FIG. 5 is a graph illustrating a relationship between an ambient temperature and a decrease in cell voltage according to the embodiment.

FIG. 6 illustrates a table based on the relationship between an ambient temperature and a decrease in cell voltage according to the embodiment.

DESCRIPTION OF EMBODIMENTS

Figure 1:
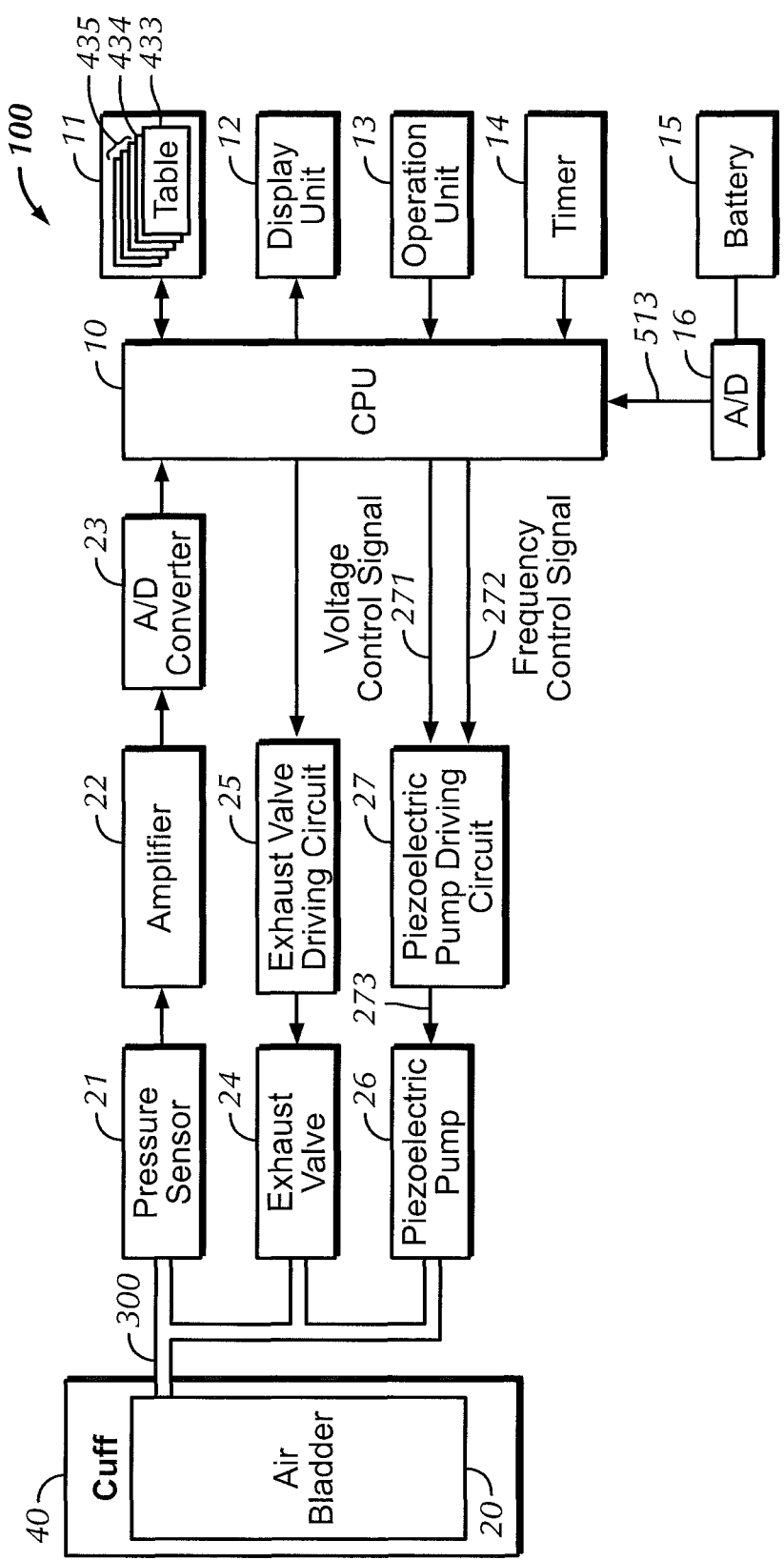
FIG. 1 is a block diagram illustrating the hardware configuration of an electronic blood pressure meter according to an embodiment.

Hereinafter, an embodiment of the present invention will be described with reference to the drawings. In the following descriptions, identical reference numerals are assigned to identical components. The names and functions thereof are also the same. Accordingly, detailed descriptions thereof will not be repeated.

FIG. 1 is a block diagram illustrating the hardware configuration of an electronic blood pressure meter 100 according to the present embodiment. As shown in FIG. 1, the electronic blood pressure meter 100 includes a cuff 40 that is attached to a blood pressure measurement area and an air system. The cuff 40 includes an air bladder 20. The air bladder 20 is connected to the air system via an air tube 300.

The electronic blood pressure meter 100 further includes a display unit 12, an operation unit 13, a CPU (central processing unit) 10 for centrally controlling various units and performing various types of computational processes, a memory 11 for storing programs for causing the CPU 10 to perform predetermined operations, various types of data, and so on, a removable battery 15 for supplying power to the respective units, and a timer 14 for carrying out time measurement operations. The memory 11 includes a non-volatile memory (for example, a flash memory) for storing a measured blood pressure. The non-volatile memory holds a table 433 searched by a circumferential length detection unit 351 (mentioned later), a table 434 searched by a decrease amount detection unit 352 (mentioned later), and a table 435 searched by a power estimation unit 35 (mentioned later).

The operation unit 13 includes a power switch for accepting operations for turning the power on or off, a measure switch for accepting an operation to start measurement, a stop switch for accepting an operation instructing the measurement to be stopped, and a user selection switch for accepting an operation that selectively specifies a user (a measurement subject). The operation unit 13 also includes a switch for accepting operations for reading out information stored in the flash memory, such as measured blood pressures, and displaying that information in the display unit.

The present embodiment assumes that the electronic blood pressure meter 100 is shared by a plurality of measurement subjects, and thus the user selection switch is provided; however, in the case where the electronic blood pressure meter 100 is not shared, the user selection switch may be omitted. In addition, the power switch may also function as the measure switch. In this case, the measure switch can be omitted.

The air system includes a pressure sensor 21 for detecting a pressure within the air bladder 20 (called a "cuff pressure" hereinafter), a piezoelectric pump 26 for supplying air to the air bladder 20 in order to increase the cuff pressure, and an exhaust valve 24 that is opened/closed in order to exhaust or inject air from/into the air bladder 20. The electronic blood pressure meter 100 also includes an amplifier 22, an A/D (analog/digital) converter 23, a piezoelectric pump driving circuit 27, and an exhaust valve driving circuit 25 used for operations involving the air system. Here, the piezoelectric pump 26, the exhaust valve 24, the piezoelectric pump driving circuit 27, and the exhaust valve driving circuit 25 correspond to an adjustment unit for adjusting the cuff pressure.

The piezoelectric pump 26 is a micro pump that uses a piezoelectric element as its driving source. The piezoelectric pump 26 includes a piezoelectric actuator driven by a vibration control voltage signal 273, a diaphragm that is layered thereupon, and a pump chamber that contracts and expands in response to the diaphragm displacing, or in other words, in response to vibrations; air is supplied to the air bladder 20 via the pump chamber that contracts and expands.

The piezoelectric pump driving circuit 27 generates and outputs the vibration control voltage signal 273 based on a voltage control signal 271 and a frequency control signal 272 from the CPU 10. The frequency control signal 272 matches a resonance frequency determined by the dimensions of the piezoelectric actuator and the diaphragm layered thereupon, and is stored in the memory 11 in advance. Meanwhile, the voltage control signal 271 indicates a voltage value determined based on the inflation speed target undergoing feedback control as described above. The piezoelectric pump driving circuit 27 generates the vibration control voltage signal 273, which is an AC voltage signal near the resonance frequency, based on the voltage control signal 271 and the frequency control signal 272, and applies the vibration control voltage signal 273 to the piezoelectric actuator.

The exhaust valve driving circuit 25 controls the opening/closing of the exhaust valve 24 based on a control signal supplied from the CPU 10.

An A/D (analog/digital) converter 16 is provided for operations involving the battery 15. The A/D converter 16 is inputted with a cell voltage of the battery 15 (an inter-terminal voltage of the battery 15), converts that voltage into digital data, and outputs a voltage signal 513 indicating a cell voltage value to the CPU 10. A non-chargeable primary battery such as a dry cell battery, or a chargeable secondary battery, can be employed as the battery 15.

The pressure sensor 21 is a electrostatic capacitance-type pressure sensor, and a capacity value thereof changes based on the cuff pressure. The pressure sensor 21 outputs a signal based on the cuff pressure to the amplifier 22. The amplifier 22 amplifies the signal inputted from the pressure sensor 21 and outputs the amplified signal to the A/D converter 23. The A/D converter 23 converts the amplified signal inputted from the amplifier 22 (an analog signal) into a digital signal and outputs the post-conversion digital signal to the CPU 10. Through this, the CPU 10 detects the cuff pressure and the pulse wave. The CPU 10 detects the cuff pressure by converting the signal obtained from the A/D converter 23 into a pressure.

Note that the fluid supplied to the cuff 40 is not limited to air, and may be a liquid, a gel, or the like. The embodiment is also not limited to a fluid, and may instead employ uniform particles such as microbeads or the like.

Functional Configuration

Figures 2, 3:
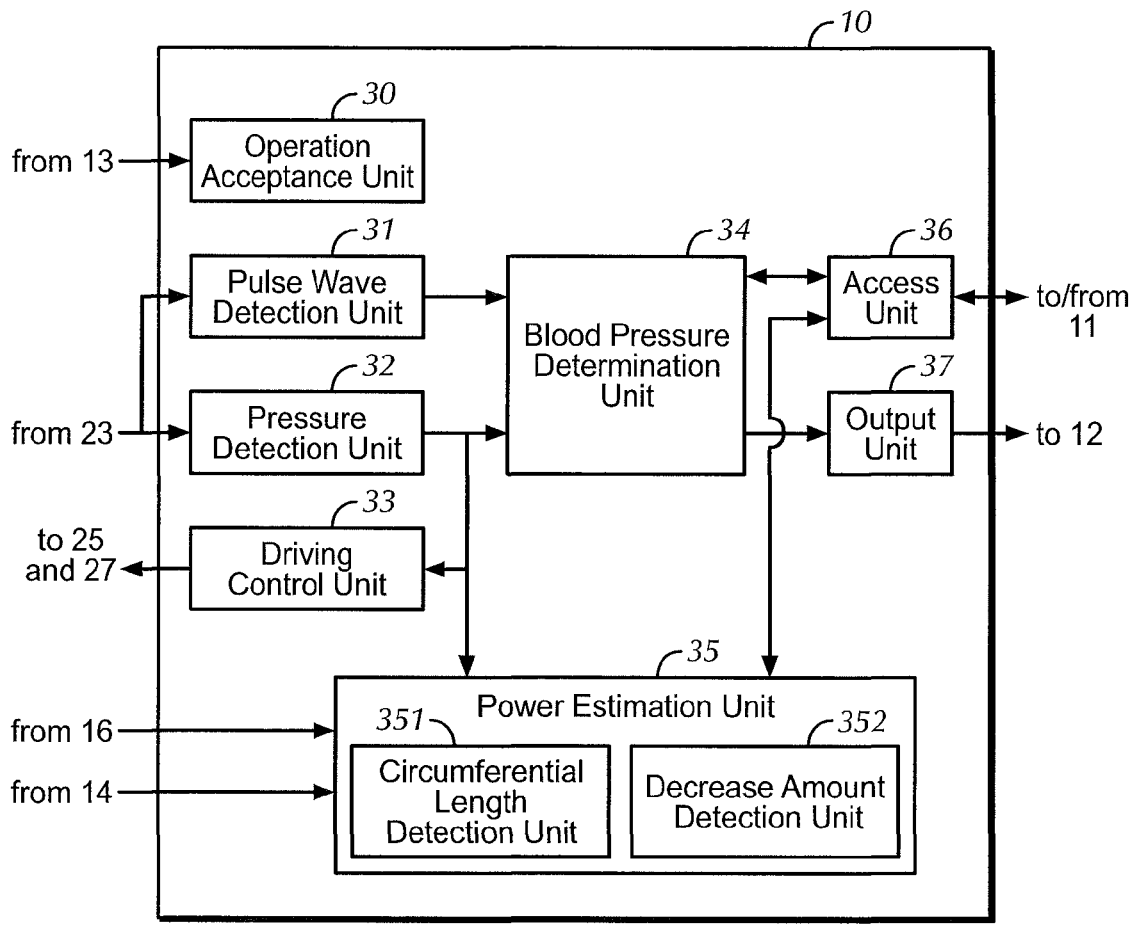
FIG. 2 is a block diagram illustrating the functional configuration of the electronic blood pressure meter according to the embodiment.
FIG. 3 illustrates an example of a table referred to in order to estimate a circumferential length according to the embodiment.

FIG. 2 is a functional block diagram illustrating the functional configuration of the electronic blood pressure meter 100 according to the present embodiment. The functional configuration illustrates the functions provided by the CPU 10 as well as related peripheral units.

As shown in FIG. 2, the CPU 10 includes: an operation acceptance unit 30 for accepting operations made by the user via the operation unit 13; a pulse wave detection unit 31 and a pressure detection unit 32 into which a pressure signal from the A/D converter 23 is inputted; a driving control unit 33 that outputs control signals to the piezoelectric pump driving circuit 27 and the exhaust valve driving circuit 25; a blood pressure determination unit 34 that determines a blood pressure value through the oscillometric technique; an access unit 36 for reading/writing data to/from (accessing) the memory 11; an output unit 37 that controls displays made in the display unit 12; and the power estimation unit 35 that estimates a voltage decrease value for the battery 15 and a consumed power amount of the electronic blood pressure meter 100.

The driving control unit 33 has a function for increasing the cuff pressure according to the inflation speed target by controlling the exhaust valve driving circuit 25 and the piezoelectric pump driving circuit 27 during blood pressure measurement. The driving control unit 33 sends control signals to the exhaust valve driving circuit 25 and the piezoelectric pump driving circuit 27 in order to adjust the cuff pressure. Specifically, control signals for increasing or decreasing the cuff pressure are outputted. In particular, the control signal for the piezoelectric pump driving circuit 27 is outputted in accordance with feedback control, which will be described later.

The pulse wave detection unit 31 detects a pulse wave signal expressing a change in the volume of an artery superimposed on the pressure signal from the A/D converter 23, using a filter circuit. The pressure detection unit 32 converts the pressure signal from the A/D converter 23 into a pressure value and outputs the pressure value in order to detect the cuff pressure.

The blood pressure determination unit 34 determines a blood pressure through a known oscillometric technique. Specifically, the blood pressure determination unit 34 determines the blood pressure based on shifts in the pulse wave amplitude and the cuff pressure, using the cuff pressure inputted from the pressure detection unit 32 during blood pressure measurement and the pulse wave detected by the pulse wave detection unit 31. For example, a cuff pressure corresponding to a maximum value of the pulse wave amplitude is set as an average blood pressure, a cuff pressure corresponding to a pulse wave amplitude on a high-cuff pressure side equivalent to 50% of the maximum value of the pulse wave amplitude is set as a systolic blood pressure, and a cuff pressure corresponding to a pulse wave amplitude on a low-cuff pressure side equivalent to 70% of the maximum value of the pulse wave amplitude is set as a diastolic blood pressure. A pulse frequency is calculated through a known procedure using the pulse wave signal. Measurement data indicating the obtained blood pressure value and pulse frequency is displayed in the display unit 12 via the output unit 37 or is stored in the memory 11 via the access unit 36. The displayed or stored measurement data may include a measurement time inputted from the timer 14.

Feedback Control of Piezoelectric Pump 26

When measuring blood pressure using the oscillometric technique, it is necessary to increase the cuff pressure at a constant inflation speed target in order to obtain an accurate measurement. In other words, the driving control unit 33 generates the voltage control signal 271 indicating a voltage based on an inflation target value as well as the aforementioned frequency control signal 272 and outputs the signals to the piezoelectric pump driving circuit 27 at the start of the blood pressure measurement. Through this, the piezoelectric pump driving circuit 27 generates the vibration control voltage signal 273 for controlling vibrations in accordance with the inflation target value, and outputs the generated signal to the piezoelectric pump 26.

After inflation has been started in accordance with an initial inflation speed target, the driving control unit 33 calculates a speed at which the cuff pressure is to be increased based on the cuff pressure inputted from the pressure detection unit 32, compares the calculated speed increase with the current inflation speed target, generates the voltage control signal 271 indicating a voltage based on a difference between the two obtained through the comparison, and outputs the generated signal to the piezoelectric pump driving circuit 27. In this manner, feedback control is carried out on the piezoelectric pump 26 using the voltage control signal 271 so that the speed at which the cuff pressure is increased reaches the inflation speed target.

The output flow rate of the piezoelectric pump 26 is proportional to the voltage indicated by the voltage control signal 271 or the frequency indicated by the frequency control signal 272 supplied from the piezoelectric pump driving circuit 27, and thus the aforementioned feedback control can be realized by changing one or both of the voltage indicated by the voltage control signal 271 and the frequency indicated by the frequency control signal 272. Here, for the sake of simplicity, it is assumed that feedback control is carried out on the piezoelectric pump 26 using the voltage control signal 271, as described above.

The power estimation unit 35 includes the circumferential length detection unit 351 that detects a circumferential length of the measurement area around which the cuff 40 is wrapped and the decrease amount detection unit 352 for detecting an amount by which the cell voltage of the battery 15 has decreased. The power estimation unit 35 estimates an amount of power consumed by the electronic blood pressure meter 100 based on the amount by which the cell voltage has decreased and the circumferential length.

Circumferential Length Estimation

Estimation of the circumferential length of the measurement area performed by the circumferential length detection unit 351 according to the present embodiment will be described next. FIG. 3 illustrates an example of the table 433 that is referred to in order to estimate a circumferential length L of the measurement area according to the present embodiment. The table 433 stores constant speed inflation times required to increase the cuff pressure by a predetermined pressure in the case where the cuff 40 is "properly wrapped" around the measurement area, along with corresponding circumferential lengths L. The data in the table 433 is obtained in advance through experimentation. FIG. 4 illustrates a graph showing cuff pressure-inflation time properties (when properly wrapped) according to the present embodiment. The data shown in FIGS. 3 and 4 indicates values based on data sampled from many measurement subjects using the electronic blood pressure meter 100. Here, "properly wrapped" refers to a state where the length of the circumference along the inner diameter of the cuff 40 when wrapped on the measurement area (that is, the diameter of a cross-section of an arm, which serves as the measurement area) is essentially the same as the circumferential length of the measurement area. The present embodiment assumes that the blood pressure is measured during the properly-wrapped state.

Here, it is assumed that the amount of air required for the cuff pressure to move from a pressure P2 to a pressure P3 is a fluid volume ΔV23, based on the cuff pressure in the cuff 40 wrapped around the measurement area and a volume change in the fluid supplied to the cuff 40 (which is air, in the present embodiment) (see FIG. 4). During the inflation process, when the piezoelectric pump 26 is carrying out constant speed inflation (where the RPM are constant), the inflation time required to supply air equivalent to the fluid volume ΔV23 is a constant time (here, a time V23 from a point in time V2 to a point in time V3). However, the time V23 changes depending on the circumferential length L of the measurement area.

For example, in the case where the cuff 40 is properly wrapped around measurement areas having different circumferential lengths, the time V23 decreases as the circumferential length decreases (with thinner arms) and the time V23 increases as the circumferential length increases (with thicker arms), as indicated in FIG. 4.

Using the timer 14, the circumferential length detection unit 351 measures an amount of time required for the cuff pressure to change from 0 mmHg (the pressure P2) to 20 mmHg (the pressure P3), based on the cuff pressure detected after the inflation has started at the initial inflation speed target. The corresponding circumferential length L is then obtained by searching the table 433 through the access unit 36 based on the measured time.

Although the circumferential length L is described here as being estimated (measured) during blood pressure measurement, the circumferential length L may be inputted by the measurement subject operating the operation unit 13 at the time of measurement. Alternatively, circumferential lengths L may be stored in the memory 11 in advance on a measurement subject-by-measurement subject basis.

Estimation of Temperature Based on Voltage Decrease Value

In the present embodiment, the cell voltage decrease value is detected in order to detect the power consumption amount. Here, an internal resistance value of the battery 15, or in other words, the voltage decrease value, will differ depending on the ambient temperature where the electronic blood pressure meter 100 is placed during use. In other words, the internal resistance of the battery 15 will increase as the ambient temperature drops, and thus even if the conditions such as the inflation speed target are the same, the cell voltage decrease value will be higher than when the ambient temperature is a normal temperature. Accordingly, in the present embodiment, the decrease amount detection unit 352 estimates the ambient temperature by detecting the cell voltage decrease value based on the voltage signal 513 at the time of the initial inflation.

FIG. 5 is a graph illustrating a relationship between the ambient temperature and the decrease in cell voltage according to the present embodiment. The graph was obtained through experiments performed by the inventors, and the vertical axis represents the cell voltage, whereas the horizontal axis represents the measurement time. According to the graph, it can be seen that the cell voltage decrease value is higher when the ambient temperature is a low temperature than when the ambient temperature is a normal temperature, even in the case where the blood pressure measurement is performed for the same circumferential length (a normal arm circumference) and the same inflation speed target.

Based on the experimental results shown in FIG. 5, the table 434 holds, in advance, various cell voltage decrease values obtained after a predetermined amount of time has passed following the start of constant speed inflation at the initial inflation speed target (that is, an amount of time required to increase the cuff pressure by a predetermined pressure) and ambient temperatures (low temperature, normal temperature, and high temperature) corresponding to the respective decrease values, as shown in FIG. 6. The predetermined amount of time essentially corresponds to the amount of time required for inflation in order to estimate the circumferential length L as described above.

Estimating Consumed Power Based on Circumferential Length

Meanwhile, based on the graph shown in FIG. 5, it can be seen that the cell voltage decrease value will increase in accordance with the circumferential length, even in the case where the blood pressure measurement is carried out at the same ambient temperature and at the same inflation speed target. Furthermore, based on the graph, it can be seen that the cell voltage decrease value will differ depending on the ambient temperature, even in the case where the blood pressure measurement is carried out using the same circumferential length and at the same inflation speed target. Thus in the present embodiment, based on the experimental results shown in FIG. 5, tables 435 shown in FIG. 7 are stored in the memory 11 for each ambient temperature (low temperature, normal temperature, and high temperature); each table 435 holds a circumferential length (short, normal, and long), as well as a voltage decrease formula for performing a calculation in order to determine the cell voltage decrease value using a time and an initial decrease value as parameters and a consumed power calculation formula for calculating an amount of consumed power, corresponding to each of the stated circumferential lengths.

The cell voltage decrease value can be calculated (estimated) by substituting the amount of time that has elapsed since the start of constant speed inflation at the initial inflation speed target in the voltage decrease formula. Accordingly, in the present embodiment, in the case where it has been determined that the battery 15 will decrease by, for example, 120% or more of the estimated cell voltage decrease value, it is determined that an abnormality is present in the piezoelectric element of the piezoelectric pump 26, or in other words, that the power consumed by the electronic blood pressure meter 100 has increased and the lifespan of the battery 15 will be shortened. In this case, notifying the measurement subject that the consumed power has increased makes it possible for the measurement subject to quickly inspect or replace the electronic blood pressure meter 100.

Figures 7, 8:
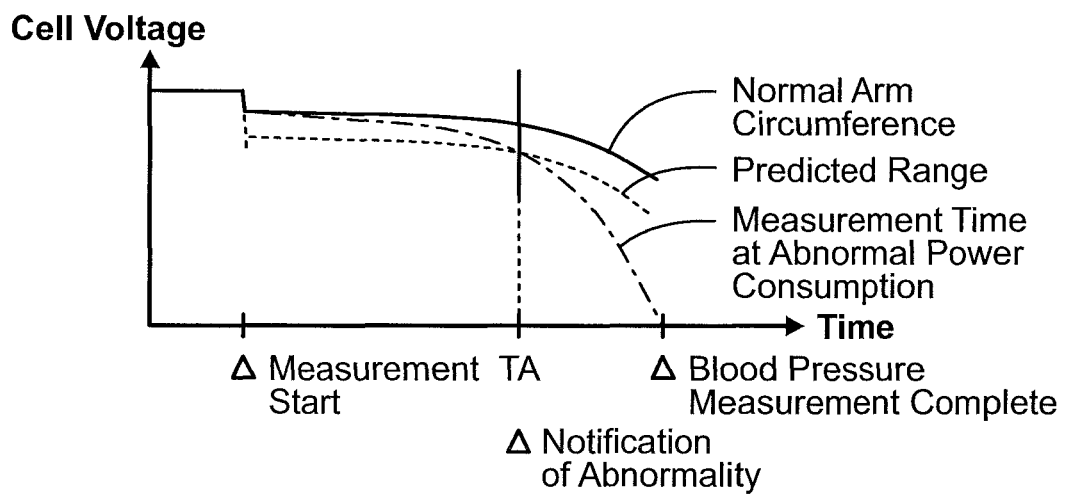
FIG. 7 illustrates a table for determining a cell voltage decrease value based on circumferential lengths for each of ambient temperatures (low temperature, normal temperature, and high temperature) according to the embodiment.
FIG. 8 is a graph illustrating a case where a value by which a cell voltage decreases is 120% or more of the estimated cell voltage decrease value, according to the embodiment.

FIG. 8 is a graph illustrating a case where it has been determined that the amount by which the cell voltage decreases is 120% or more of the estimated cell voltage decrease value, according to the present embodiment. In this graph, the vertical axis represents the cell voltage, whereas the horizontal axis represents the amount of time elapsed in the blood pressure measurement. In FIG. 8, a change in the voltage decrease value over time for the case where the blood pressure is measured under conditions in which the temperature is a normal temperature and the circumferential length L is a normal length is graphed as a solid line, and the case where the cell voltage decreases by 120% of the stated decrease value is graphed as a broken line, as examples. Here, the broken-line graph will be referred to as a "predicted range" of the voltage decrease. Accordingly, in the case where a voltage decrease value such as that indicated by the dot-dash line graph has been measured during the actual blood pressure measurement, it is determined that the voltage decrease value measured in a time TA following the start of the blood pressure measurement is less than the "predicted range", and the measurement subject is notified that an abnormally large amount of power is being consumed. Here, the voltage decrease formula in the table 435 is an arithmetic equation obtained through experimentation, by obtaining graphs (corresponding to the broken-line graph in FIG. 8) for the "predicted range" from experimental cases using different circumferential lengths L and ambient temperatures, and performing curve approximation on the obtained graphs.

Flowchart

Figure 9:
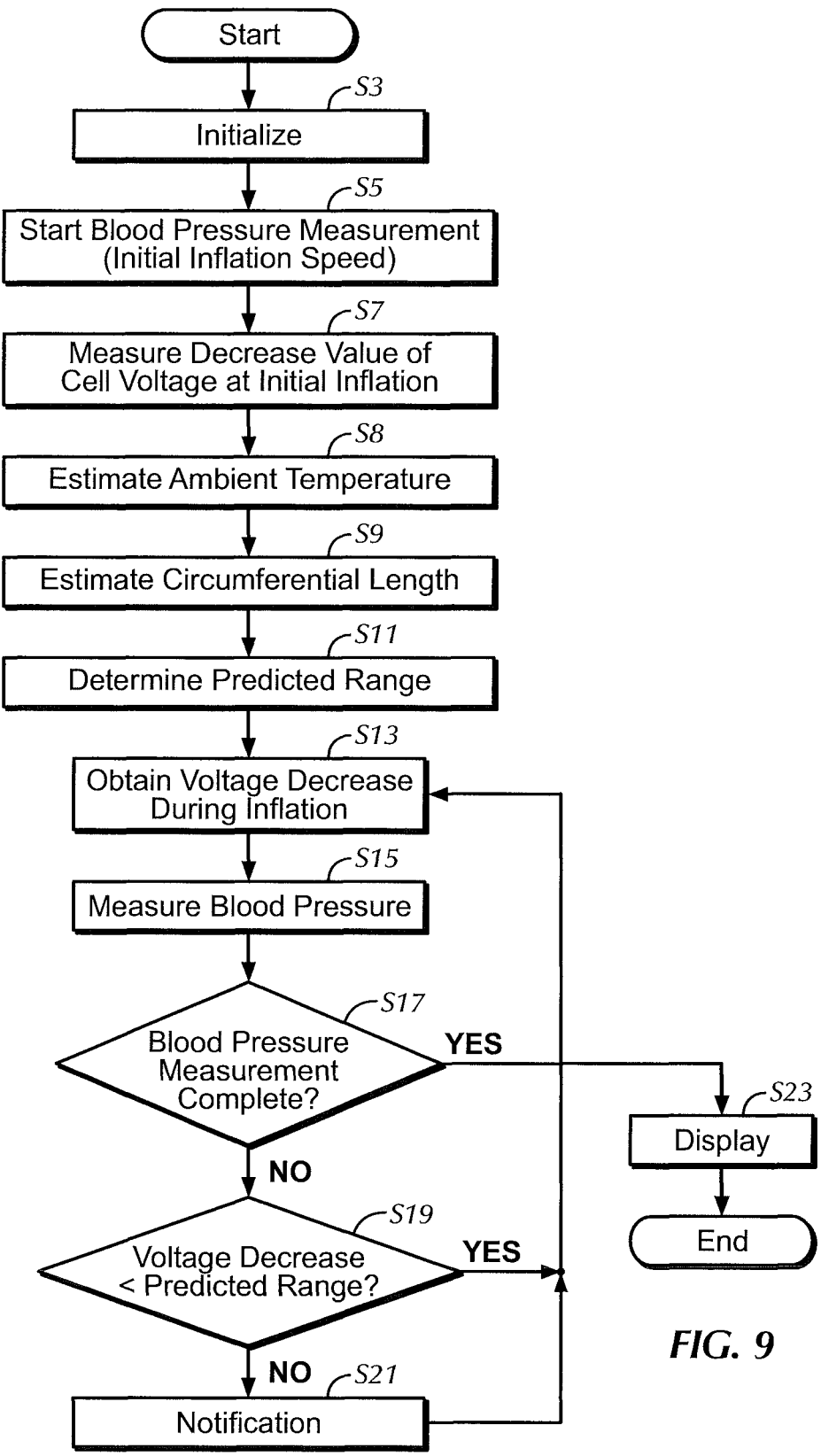
FIG. 9 is a flowchart illustrating a blood pressure measurement process according to the embodiment.

FIG. 9 is a flowchart illustrating a blood pressure measurement process according to the present embodiment. A program represented by this flowchart is stored in advance in the memory 11, and is read out from the memory 11 and executed by the CPU 10.

When the measurement subject manipulates the power switch (or the measure switch) of the operation unit 13 while the cuff 40 is properly wrapped around the measurement area, the corresponding operation is accepted by the operation acceptance unit 30, and a signal instructing measurement to start is outputted in accordance with the accepted operation. An initialization process is carried out in response to the instruction signal (step S3). Specifically, the power estimation unit 35 takes the voltage signal 513 as an input and detects an initial decrease value, which corresponds to an initial cell voltage. Meanwhile, the driving control unit 33 outputs the voltage control signal 271 and the frequency control signal 272 to the piezoelectric pump driving circuit 27, and outputs a control signal for closing the exhaust valve 24 to the exhaust valve driving circuit 25. The exhaust valve 24 is closed by the exhaust valve driving circuit 25 as a result.

The piezoelectric pump driving circuit 27 generates the vibration control voltage signal 273 based on the inputted voltage control signal 271 and frequency control signal 272, and outputs the vibration control voltage signal 273 to the piezoelectric pump 26. As a result, the piezoelectric pump 26 operates so as to increase the cuff pressure at a constant speed in accordance with an initial inflation speed target (for example, 5.5 mmHg/sec) at the time when the blood pressure measurement is started (step S5).

When it has been determined, using the timer 14, that a predetermined amount of time has passed since the constant speed inflation was started, the decrease amount detection unit 352 detects a value by which the voltage has decreased from the initial decrease value based on the voltage signal 513 (step S7). The table 434 in the memory 11 is then searched based on the detected voltage decrease value, and temperature data corresponding to a result of the search is read out (step S8). The ambient temperature is estimated as a result.

Meanwhile, after the constant speed inflation has started, the circumferential length estimating unit 351 estimates the circumferential length L according to the aforementioned procedure (step S9).

The power estimation unit 35 searches the memory 11 based on the estimated ambient temperature, and identifies the table 435 corresponding to the ambient temperature obtained through the search. Then, the identified table 435 is searched based on the estimated circumferential length L, and the corresponding voltage decrease formula obtained as a result of the search is read out (step S11). Through this, the arithmetic equation for calculating the "predicted range" can be obtained.

The power estimation unit 35 estimates the cell voltage based on the voltage signal 513 in parallel with the constant speed inflation (step S13). Meanwhile, the blood pressure is estimated through the oscillometric method by the blood pressure determination unit 34 (step S15), and when it is determined that the blood pressure has been determined and the measurement is complete (YES in step S17), the driving control unit 33 outputs control signals to stop the piezoelectric pump 26 and open the exhaust valve 24. As a result, the air is exhausted from the air bladder 20 and the cuff pressure decreases. The measurement result is then stored in the memory 11 and displayed in the display unit 12 (step S23), after which the process ends.

While the cuff is not sufficiently inflated, the blood pressure cannot be determined (NO in step S17), and thus the process advances to step S19.

The power estimation unit 35 calculates the voltage decrease value from the initial value based on the initial cell voltage measured in step S3 and the current cell voltage indicated by the voltage signal 513, and determines whether or not the calculated current voltage decrease value is less than the "predicted range" calculated through the voltage decrease formula read out in step S11. Here, the value of the initial cell voltage measured in step S3 and the measurement time measured by the timer 14 are substituted as parameters in the voltage decrease formula, and the voltage decrease value based on that voltage decrease formula is calculated as the "predicted range". Because the flow rate properties of the piezoelectric element in the piezoelectric pump 26 change depending on the ambient temperature, a coefficient that is dependent on the ambient temperature is included in the parameters of the voltage decrease formula.

When the power estimation unit 35 determines that the current voltage decrease value is less than the "predicted range" (YES in step S19), the process returns to step S13 and the processes that follow thereafter are performed in the same manner; however, when it is determined that the current voltage decrease value is greater than or equal to the "predicted range" (NO in step S19), the power estimation unit 35 makes a notification, via the output unit 37, that the consumed power amount is too great (step S21). Thereafter, the process returns to step S13, and the processes that follow thereafter are repeated.

Note that when it has been determined that the consumed power is too great, that determination result may be stored in the memory 11 in association with a result of the blood pressure measurement. Through this, information indicating that a piezoelectric pump 26 experiencing an excessive voltage decrease cannot be controlled properly and thus the accuracy of the blood pressure measurement cannot be ensured can be stored, or can be displayed along with measurement results.

First Variation

It is generally known that an increase in the voltage decrease value is accompanied by an increase in the consumed power amount, and thus the voltage decrease value (called a "voltage decrease value $\Delta V$" hereinafter) is measured (detected) and an excessive consumed power amount is determined using the voltage decrease value $\Delta V$ and communicated to the measurement subject in the aforementioned embodiment; however, instead of or along with this operation, the power estimation unit 35 may calculate the consumed power amount from the measured voltage decrease value using a predetermined arithmetic equation, determine the level of the calculated consumed power amount, and notify the measurement subject of a result of the determination. In this case, the "predicted range" corresponds to the consumed power amount calculated through the predetermined arithmetic equation using the voltage decrease value ΔV indicated by the broken-line graph in FIG. 8.

The consumed power calculation formula corresponding to the circumferential length may then read out from the table 435 in order to calculate the consumed power amount, and may be used as the aforementioned predetermined arithmetic equation. The predetermined arithmetic equation for calculating the consumed power may be, for example, $W = \Delta V \times \alpha + \beta$. Here, W represents the consumed power amount; because the voltage decrease value ΔV changes depending on the ambient temperature, α and β represent predetermined coefficient values that are dependent on the ambient temperature.

Second Variation

Although the aforementioned embodiment describes detecting the ambient temperature after the start of the blood pressure measurement, the ambient temperature may be measured by measuring the voltage decrease value of the battery 15 using a reference resistance prior to the start of the blood pressure measurement. Alternatively, a temperature sensor may be provided and the ambient temperature may be measured by the temperature sensor.

Third Variation

In the aforementioned embodiment, the driving control unit 33 controls the inflation speed by performing feedback control on the piezoelectric pump 26 using the voltage control signal 271. In the feedback control, the driving control unit 33 varies the voltage value indicated by the voltage control signal 271 within a range that is greater than a BL ("battery low") voltage value set for the battery 15.

Here, BL ("battery low") refers to a required voltage determined in accordance with the design specifications of the electronic blood pressure meter 100, and specifies a cell voltage required in order to ensure that the electronic blood pressure meter 100 operates normally. Data specifying a set value for the BL voltage indicates a value at normal temperature, and is stored in advance in the memory 11.

Figure 10:
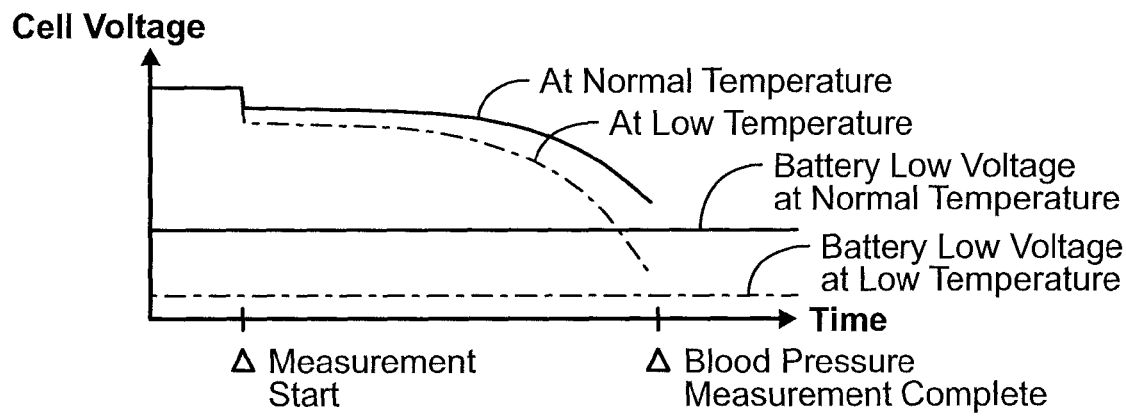
FIG. 10 is a diagram illustrating variation of a BL voltage in accordance with an ambient temperature according to the embodiment.

However, because the internal resistance value of the battery 15 changes depending on the ambient temperature as described above, the BL voltage may also be varied in accordance with the ambient temperature as illustrated in FIG. 10. FIG. 10 is a graph illustrating an example of changes in the BL voltage based on the ambient temperature, according to the present variation.

The vertical axis in FIG. 10 represents the cell voltage, whereas the horizontal axis represents the amount of time that has elapsed in the blood pressure measurement. There is a more marked voltage decrease in the battery 15 at the low temperature than at the normal temperature, and thus in the case where a BL voltage for the normal temperature is used for a blood pressure measurement carried out at a low temperature, the voltage decrease value of the battery 15 will exceed the BL voltage before the blood pressure measurement is complete, making it difficult to carry out precise feedback control.

Accordingly, the value of the BL voltage at the low temperature is set to be lower than the value of the BL voltage at the normal temperature. Through this, the feedback control can be carried out within the voltage range indicated by the BL voltage until the blood pressure measurement is complete, even at the low temperature.

Meanwhile, although the aforementioned embodiment describes determining the frequency of the frequency control signal 272 in accordance with the size of the piezoelectric element, changes in the size (expansion/contraction) resulting from the ambient temperature may be taken into consideration and the frequency of the frequency control signal 272 may also be varied in accordance with the ambient temperature.

Fourth Variation

Figure 11:
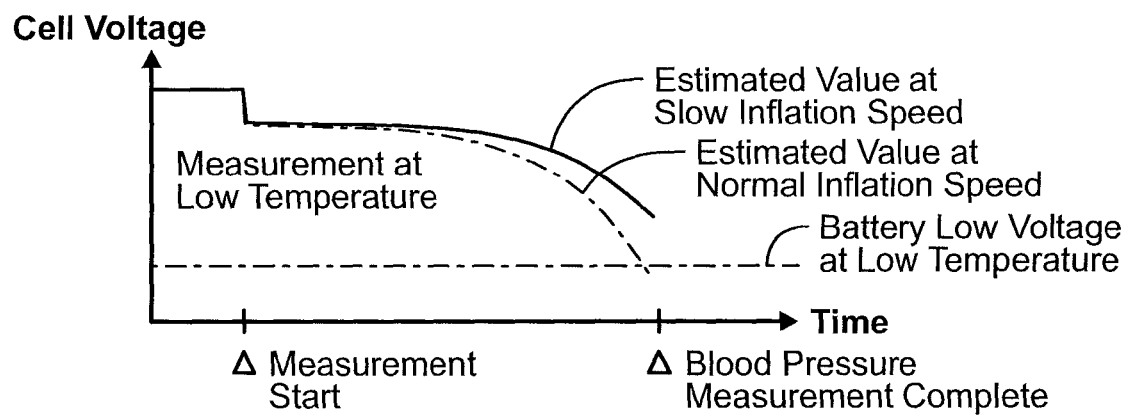
FIG. 11 is a diagram illustrating variation of an initial inflation voltage in accordance with an ambient temperature according to the embodiment.

In addition, although the aforementioned embodiment describes determining the initial inflation voltage indicated by the voltage control signal 271 supplied to the piezoelectric pump 26 so that the inflation speed target (for example, 5.5 mmHg/sec) is attained, the initial inflation voltage may also be varied in accordance with the ambient temperature, as indicated in FIG. 11.

The vertical axis in FIG. 11 represents the cell voltage, whereas the horizontal axis represents the amount of time that has elapsed in the blood pressure measurement. There is a more marked voltage decrease in the battery 15 at the low temperature than at the normal temperature, and thus in the case where the cuff is inflated at the inflation speed target for the normal temperature when carrying out blood pressure measurement at the low temperature, the voltage decrease value of the battery 15 will exceed the BL voltage for the low temperature before the blood pressure measurement is complete, making it difficult to carry out precise feedback control.

Accordingly, the ambient temperature is detected at the initial inflation when starting the blood pressure measurement, and changes in the flow rate properties of the piezoelectric element resulting from the ambient temperature are taken into consideration; the inflation voltage for determining the inflation speed target in the following inflation process may then be varied depending on the ambient temperature. In FIG. 11, the inflation voltage for the low temperature is set to be lower than for the normal temperature. Through this, the feedback control can be carried out within the voltage range indicated by the BL voltage until the blood pressure measurement is complete, even at the low temperature.

In addition, although the aforementioned embodiment describes determining the circumferential length L based on the amount of time required to inflate the cuff by a predetermined pressure, varying the inflation voltage based on the ambient temperature in this manner makes it possible to determine the circumferential length L with a high degree of accuracy.

Fifth Variation

Different types of batteries can be used for the battery 15. Because the voltage decrease amount differs depending on whether a secondary battery or a primary battery (a dry cell battery) is used as the battery 15, the measurement subject may input the type of the battery 15 in advance using the operation unit 13, and the power estimation unit 35 may change the "predicted range" depending on the type of the battery inputted by the measurement subject. Alternatively, instead of an input operation, the ambient temperature may be measured based on a reference resistance and whether the battery 15 is a secondary battery or a primary battery (a dry cell battery) may then be determined based on a voltage decrease amount caused by the blood pressure measurement.

Note that the embodiments disclosed above are to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

REFERENCE SIGNS LIST 26 piezoelectric pump
27 piezoelectric pump driving circuit
31 pulse wave detection unit
32 pressure detection unit
33 driving control unit
34 blood pressure determination unit
35 power estimation unit
100 electronic blood pressure meter 271 voltage control signal
272 frequency control signal
273 vibration control voltage signal
351 circumferential length detection unit
352 decrease amount detection unit
433, 434, 435 table
513 voltage signal

The invention claimed is:

1. An electronic blood pressure meter comprising:
   a cuff to be wrapped around a measurement area of a measurement subject;
   an adjustment unit that adjusts a pressure in the cuff by controlling a piezoelectric pump that uses a piezoelectric vibrator to supply a fluid to the cuff;
   a driving control unit that gradually changes the pressure in the cuff by performing driving control on the adjustment unit;
   a pressure detection unit that detects a cuff pressure indicating the pressure in the cuff;
   a blood pressure determination unit that determines a blood pressure value based on the cuff pressure detected by the pressure detection unit;
   a circumferential length detection unit that detects a circumferential length of the measurement area;
   a battery that supplies power to various units; and
   a decrease detection unit that detects a voltage decrease value for the battery during blood pressure measurement,
   wherein based on the circumferential length and the voltage decrease value detected in an initial inflation period when the blood pressure measurement is first started, a range of the voltage decrease value during the blood pressure measurement carried out thereafter is estimated, and
   wherein the detected voltage decrease value differs depending on an ambient temperature.

2. The electronic blood pressure meter according to claim 1,
   wherein when it is determined that the detected voltage decrease value exceeds the range, an output to that effect is made.

3. The electronic blood pressure meter according to claim 1,
   wherein based on the circumferential length and the voltage decrease value detected in the initial inflation period when the blood pressure measurement is first started, a range of a consumed power amount during the blood pressure measurement carried out thereafter is estimated.

4. The electronic blood pressure meter according to claim 3,
   wherein the consumed power amount is estimated based on the detected voltage decrease value, and when it is determined that the estimated consumed power amount exceeds the range, an output to that effect is made.

5. The electronic blood pressure meter according to claim 1,
   wherein the range is varied based on a detected relative ambient temperature around the electronic blood pressure meter.

6. The electronic blood pressure meter according to claim 5,
   wherein the relative ambient temperature is detected based on the voltage decrease value detected by the decrease detection unit when the cuff pressure is increased by a predetermined pressure.

7. The electronic blood pressure meter according to claim 6,
   wherein the relative ambient temperature is detected based on the voltage decrease value detected by the decrease detection unit when the cuff pressure is increased by a predetermined pressure during the initial inflation period when the blood pressure measurement is first started.

8. The electronic blood pressure meter according to claim 1,
   wherein the circumferential length detection unit detects the circumferential length based on an amount of time required to inflate the cuff pressure by a predetermined pressure during the initial inflation period when the blood pressure measurement is first started.

9. The electronic blood pressure meter according to claim 1,
   wherein a speed at which the cuff pressure is increased by the driving control unit through the adjustment unit is varied based on the voltage decrease value detected by the decrease detection unit when the cuff pressure is increased by a predetermined pressure during the initial inflation period when the blood pressure measurement is first started.

10. The electronic blood pressure meter according to claim 1,
    wherein the battery is one of a primary battery and a secondary battery, and
    wherein the range is varied in accordance with the type of the battery.

11. The electronic blood pressure meter according to claim 10,
    wherein the type is determined based on the voltage decrease value detected by the decrease detection unit when the cuff pressure is increased by a predetermined pressure.

12. A method of controlling a blood pressure meter employing a piezoelectric pump that uses a piezoelectric vibrator to supply a fluid to a cuff wrapped around a measurement area of a measurement subject, the method comprising:
    gradually changing a pressure in the cuff by controlling the piezoelectric pump in order to measure a blood pressure;
    detecting a circumferential length of the measurement area;
    detecting a voltage decrease value for a battery that supplies power to various units of the blood pressure meter, during blood pressure measurement; and
    estimating, based on the circumferential length and the voltage decrease value detected in an initial inflation period when the blood pressure measurement is first started, a range of the voltage decrease value during the blood pressure measurement carried out thereafter,
    wherein the detected voltage decrease value differs depending on an ambient temperature.

* * * * *